United States Patent
Jabourian

(10) Patent No.: US 10,692,604 B2
(45) Date of Patent: Jun. 23, 2020

(54) DETERMINATION OF UNSUSPECTED ARRHYTHMIA BASED ON EXTRA-CARDIAC SIGNS

(71) Applicant: Artin Pascal Jabourian, Santa Barbara, CA (US)

(72) Inventor: Artin Pascal Jabourian, Santa Barbara, CA (US)

(*) Notice: Subject to any disclaimer, the term of this patent is extended or adjusted under 35 U.S.C. 154(b) by 336 days.

(21) Appl. No.: 15/533,984

(22) PCT Filed: Dec. 8, 2015

(86) PCT No.: PCT/US2015/064522
§ 371 (c)(1),
(2) Date: Jun. 7, 2017

(87) PCT Pub. No.: WO2016/094417
PCT Pub. Date: Jun. 16, 2016

(65) Prior Publication Data
US 2018/0336969 A1 Nov. 22, 2018

Related U.S. Application Data

(60) Provisional application No. 62/089,141, filed on Dec. 8, 2014.

(51) Int. Cl.
*G16H 50/30* (2018.01)
*A61B 5/00* (2006.01)
(Continued)

(52) U.S. Cl.
CPC ............ *G16H 50/30* (2018.01); *A61B 5/112* (2013.01); *A61B 5/7275* (2013.01); *G06F 19/00* (2013.01); *A61B 5/681* (2013.01); *A61B 5/6898* (2013.01)

(58) Field of Classification Search
CPC ...................................... A61B 5/112
See application file for complete search history.

(56) References Cited

U.S. PATENT DOCUMENTS 4,409,985 A 10/1983 Sidorenko et al.
5,695,343 A 12/1997 Jabourian
(Continued)

FOREIGN PATENT DOCUMENTS

DE 3120309 A1 12/1982
EP 2661225 A1 11/2013
(Continued)

OTHER PUBLICATIONS

European Patent Office, Extended European Search Report which issued in related European Patent Application No. 15868580.0 dated Jun. 7, 2018 (10 pages).
(Continued)

*Primary Examiner* — Scott Luan
(74) *Attorney, Agent, or Firm* — Laura M. King; Matrix Law Group, LLP

(57) ABSTRACT

The invention relates to a system for determining the risk of cardiac arrhythmia in an individual. This system comprises the measurement of physical parameters (VA, VB, VC, D1, Vequ) of the individual and comparing the measured physical parameters (VA, VB, VC, D1, Vequ) with physical reference parameters (VAref, VBref, D1ref, VequRef). A statistical correspondence between the cardinal parameters (C1-C6) and a level of risk of arrhythmia is selected. The risk of arrhythmia in the individual is determined from the statistical correspondence and a previously selected number of cardinal parameters corresponding to extra-cardiac parameters.

10 Claims, 9 Drawing Sheets

(51) Int. Cl.
G06F 19/00 (2018.01)
A61B 5/11 (2006.01)

(56) References Cited

U.S. PATENT DOCUMENTS

| | | | |
|---|---|---|---|
| 7,123,953 B2 | 10/2006 | Starobin et al. | |
| 7,177,684 B1* | 2/2007 | Kroll | A61B 5/1112 600/595 |
| 2003/0130586 A1* | 7/2003 | Starobin | A61B 5/0464 600/515 |
| 2006/0147450 A1* | 7/2006 | Shelton | C07K 16/22 424/145.1 |
| 2012/0196257 A1 | 8/2012 | Verghese et al. | |

FOREIGN PATENT DOCUMENTS

| | | |
|---|---|---|
| FR | 2731340 A1 | 9/1996 |
| FR | 2961085 B1 | 12/2011 |
| FR | 2969917 B1 | 7/2012 |
| FR | 2977137 B1 | 10/2013 |
| WO | 2011063092 A1 | 5/2011 |
| WO | 2012093143 A1 | 7/2012 |
| WO | 2013087104 A1 | 6/2013 |

OTHER PUBLICATIONS

USPTO International Searching Authority, International Search Report and Written Opinion issued in parent International Patent Application No. PCT/US2015/064522 dated Jun. 13, 2016, 7 pages.

Afilalo et al., "Addition of Frailty and Disability to Cardiac Surgery Risk Scores Identifies Elderly Patients at High Risk of Mortality or Major Morbidity," Circ. Cardiovasc Qual Outcomes, 2012; 5:222-228; downloaded at http://circoutcomes.ahajournals.org on Feb. 5, 2015.

Afilalo et al., "Gait Speed as an Incremental Predictor of Mortality and Major Morbidity in Elderly Patients Undergoing Cardiac Surgery," Journal of the American College of Cardiology, vol. 56, No. 20, Nov. 9, 2010:1668-76, Pub. Elsevier Inc.

Ajayi et al., "Symptom-limited, self-paced walking in the assessment of cardiovascular disease in patients with and without heart failure: the predictive value of clinical, anthropometric, echocardiographic and ergonometric parameters," Int. Journal of Cardiology, Nov. 1991, vol. 33, Issue 2, pp. 233-240, downloaded from http://www.internationaljournalofcardiology.com/article/0167-5273(91)9035 . . . on Feb. 5, 2015.

Hausdorff et al., "A new technique for simultaneous monitoring of electrocardiogram and walking cadence," The American Journal of Cardiology, vol. 70, Issue 11, Oct. 15, 1992, pp. 1064-1071; downloaded from http://www.sciencedirect.com/science/article/pii/0002914992903623 on Feb. 5, 2015.

Hausdorff, J. M., "Gait Dynamics, Fractals and Falls: Finding Meaning in the Stride-to-Stride Fluctuations of Human Walking," NIH Public Access, pp. 1-45; Hum Mov Sci. Author manuscript; available in PMC Aug. 1, 2008.

Hausdorff, J. M., "Gait variability: methods, modeling and meaning," Journal of NeuroEngineering and Rehabilitation 2005, 2:19; http://www.jneuroengrehab.com/content/2/1/19 (9 pages).

Hausdorff et al., "Increased Walking Variability in Elderly Persons With Congestive Heart Failure," JAGS vol. 42, No. 10, pp. 1056-1061, Oct. 1994; pub. Am. Geriatrics Soc.

Jabourian A.P., "Cognitive functions, EEG and gait disorders in cardiac arrhythmias, one day before and eight days after pacemaker implantation," English Abstract of French Article titled "Fonctions Cognitives, EEG Et Troubles de La Marche Dans Les Arythmies Cardiaques, Un Jour Avant et Huit Jours Apres L'Implantation D'un Stimulateur Cardiaque," Extrait d'Annales Medico-Psychologiques, 1995, 153, N. 2.

Jabourian et al., "Gait Velocity Is an Indicator of Cognitive Performance in Healthy Middle-Aged Adults," PLOS One, www.plosone.org, Aug. 2014, vol. 9, Issue 8, pp. 1-13.

Journal of Neurology, Abstracts of vol. 257, Issue 3, pp. 392-398, Sep. 26, 2009; vol. 261, Issue 10, pp. 1992-1298, Jul. 22, 2014; vol. 252, Issue 3, pp. 300-306, Feb. 23, 2005.

Kobayashi et al., "Telemetry System of Daily Life Motion and Arrhythmia," Proceedings—19th International Conference—IEEE/EMBS Oct. 30-Nov. 2, 1997 Chicago, IL. USA, pp. 2229-2231.

Rubenstein L. Z., "Falls in older people: epidemiology, risk factors and strategies for prevention," Age and Ageing 2006; 35-S2: ii37-ii41; doi:10.1093/ageing/afl084.

Salzman, B., "Gait and Balance Disorders in Older Adults," American Family Physician, Jul. 1, 2010, vol. 82, No. 1, pp. 61-68; www.aafp.org/afp.

Verghese et al., "Motoric Cognitive Risk Syndrome and the Risk of Dementia," J Gerontol A Biol Sci Med Sci. Apr. 1, 2013;68(4):412-418.

Viriyavejakul, A. et al., "Epidemiology of stroke in the elderly in Thailand," Abstract, downloaded from http://europepmc.org/abstract/med/976086, Feb. 5, 2015, 3 pages.

* cited by examiner

DETERMINATION OF UNSUSPECTED ARRHYTHMIA BASED ON EXTRA-CARDIAC SIGNS

CROSS-REFERENCE TO RELATED APPLICATIONS

The present Application is a national stage of International Patent Application No. PCT/US2015/064522, titled "Determination of Unsuspected Arrhythmia Based on Extra Cardiac Signs," filed Dec. 8, 2015, which claims the benefit of U.S. Provisional Patent Application No. 62/089,141 titled "Methods and System to Determine the Risk of Arrhythmia or Cognitive Impairment Based on Extra-Cardiac Signs," filed Dec. 8, 2014, the contents of which are incorporated herein by reference in their entirety.

BACKGROUND

Cardiac arrhythmias can cause three types of cerebral disorders. The first, and most well-known, are strokes. The second disorder is insidious cognitive decline. Identification of cognitive decline is challenging because of the identification of the decline, the transient arrhythmia involved and the mutual link between them. The third, less well known type of cerebral disorder is psychiatric disorder. Since psychiatric disorders are less well known, characterization is difficult.

Sudden cardiac death affects 400,000 to 500,000 individuals each year in the United States and Europe. A quarter of these deaths occur in patients with no history of cardiac disease and with seemingly structurally and functionally healthy hearts.

Epidemiological data indicate that psychiatric patients, especially those with depressive and/or anxiety disorders, have a high risk of cerebro-cardiovascular events and sudden cardiac death, even in the absence of documented coronary artery disease. A prospective study of phobic anxiety in 3,000 health professionals demonstrated that the relative risk of sudden cardiac death was 6.08 times higher in this population. Weissman, M M, Markowitz, J S, Ouellette, R, Greenwald, S, Kahn, J. P (1990), *Panic disorder and cardiovascular/cerebrovascular problems: Results from a community survey*, Am. J. of Psychiatry, 147, (11), 1504-1508. Additionally, emotional, physiological and physical stresses are associated with increased levels of risk of cardiac arrhythmia and sudden death. In addition, unknown cardiac arrhythmia can cause brain disorders such as Cerebral Vascular Accident (CVA) or insidious cognitive deficits. Some anxiety disorders may be manifestations of true unknown or underestimated cardiac arrhythmias De Jaeger C, Jabourian A P, Findji G, Armenian G, Champart-Curie O (1994), *Altered cognitive functions in a population of elderly people hospitalized for fall related fractures*, J Am Geriatr. Soc. 42: 1305; Jabourian A P, de Jaeger C, Findji G, Armenian G, Haddad A (1994), *Cognitive functions and fall-related fractures*, Br J Psychiatry 165: 122; Jabourian A P (1995), *Cognitive Functions, EEG and Gait Disorders in Cardiac Arrhythmias, One Day Before and Eight Days After Pacemaker Implantation*, Ann. Med. Psychol. 153: 89-105; Jabourian A, Lancrenon S, Delva C, Perreve-Genet A, Lablanchy J-P, et al. (2014), *Gait Velocity as an Indicator of Cognitive Performance in Healthy Middle-Aged Adults*, PLoS ONE 9(8): e103211; see also U.S. Pat. No. 5,695,343, EP Patent Application 2661225, French Patent Application Publication 2961085, PCT Patent Publication WO2012093143, PCT Patent Publication WO2013087104.

The paroxysmal character of many cardiac arrhythmias makes arrhythmic events difficult to recognize and diagnose. A means for recording arrhythmic events with ambulatory devices or insertable loop recorders (ILR) allows cardiac monitoring over a 14 month period. However, these methods and devices to detect cardiac arrhythmias and assess the risk of potential life-threatening arrhythmia are based solely on cardiac criteria such as history or current heart disease with altered electro-cardiograms such as long PR and premature ventricular contractions. Moreover, syncope of unknown etiology and vaso-vagal syncopes with anxiety disorders are not systematically included in these criteria. Only 1% of patients meeting the cardiac criteria received an ILR. There are no guidelines for diagnosing patients complaining of anxiety disorders and "subjective" cardio-respiratory symptoms such as chest pain, difficulty breathing, palpitations and malaise, presyncope and/or syncope. In the best of cases, such patients receive standard cardiovascular tests such as EKG or ECHO, but arrhythmic events are not monitored.

These subjective symptoms are also present in a large percentage of patients suffering from panic attacks. As such, there is an unfortunate tendency for physicians to ascribe these subjective symptoms to anxiety. However, the subjective symptoms may also be manifestations of a life-threatening cardiac arrhythmia. Consequently, it is difficult to determine among psychiatric patients, especially in patients with anxiety and depressive disorders, those patients who are at risk of arrhythmia with multiple severe complications, including strokes, epilepsy, intellectual decline, dementia and sudden death.

Moreover, many psychotropic drugs are proarrhythmogenic and require a preventive rhythm study before their administration. However, the study is rarely or never done. The neuropsychiatric assessment of more than three thousands patients suffering from cardiac arrhythmia in four Parisian clinics revealed that 70% of the patients had a cognitive and walking speed decline associated with EEG disorders, falls, dizzy spells, history and/or presence of anxiodepressive disorders. These symptoms were confirmed by a corollary study.

Thus, there is a need to monitor cardiac and rhythmic patterns in patients with anxiety disorders and subjective cardio-respiratory symptoms, including chest pain, difficulty breathing, palpitations and malaise, presyncope and/or syncope, as well as other extra-cardiac pathologies in order to determine patients who are at risk of cardiac disease and arrhythmia.

The system and method of the invention can detect the risk of cardiac arrhythmia in populations who present one or more subjective disorders, or in patients with extra-cardiac pathologies. The system and method of the invention can also detect individuals at risk of cerebro-cardiovascular events such strokes, coronary and other arteries diseases, the presence or risk of cognitive impairment, and the risk of sudden cardiac death.

The invention comprises a system and method to measure and compare the walking speed of an individual depending on the individual's walking speed in order to determine the individual's propensity for the development or presence of cognitive impairment, the risks of cardiac arrhythmia, cerebral and or vascular events, and sudden cardiac death.

SUMMARY

The current invention is a method and apparatus for detecting the risk of an individual having or developing cardiac arrhythmia based on extra cardiac signs. The method includes measuring one or more physical parameters in the individual, the physical parameters chosen from the group comprising the individual's usual walking speed (VA), the individual's fast walking speed (VB), the individual's fast walking speed while the user performs a cognitive task (VC), and the individual's equilibrium parameters (Vequ). The physical parameters are compared, alone or in combination, with physical parameters reference values (VAref, VBref, VCref, D1ref). A statistical correspondence between the risk factors and a risk of an individual having or developing cardiac arrhythmia is determined. The number of risk factors in the individual is determined, and the risk of an individual having or developing cardiac arrhythmia is calculated based on the individual's walking speed and number of risk factors. In this way, the risk of an individual having or developing cardiac arrhythmia is determined. It is contemplated that the risk factors comprise cardinal parameters, such as, for example, anxiety, depressive disorders, panic attacks, heart palpitations, choking sensation, chest pain, modification of sensory perception, cold sensation in the extremities, sexual dysfunction, decrease of libido, erectile dysfunction, a physical disorder, a mental disorder, neurophysiological abnormalities, brain abnormality, seizures and their frequency, syncope; and unexplained falls. In one aspect, the method can be performed on an electronic device. It is contemplated that the electronic device is a smart phone, smart watch or tablet computer. In one aspect, the statistical correspondence between the risk factors and a risk of an individual having or developing cardiac arrhythmia is taken from the Iglob index.

In another embodiment of the invention, an apparatus is used for determining a risk of arrhythmia in an individual. The electronic apparatus has a display and a sensor used to measure one or more physical parameters in the individual, the physical parameters chosen from the group comprising the individual's usual walking speed (VA), the individual's fast walking speed (VB), the individual's fast walking speed while the user performs a cognitive task (VC), and the individual's equilibrium parameters (Vequ). The apparatus also has a means for storing the physical parameters in a data memory, as well as a means to compare the measured physical parameters with reference to physical parameters such as usual walking speed reference (VAref), fast walking speed reference (VBref), and an equilibrium parameter reference (VequRef). The apparatus also contains a means for inputting the number of risk factors present in the individual, a means to determine the statistical correspondence between one or more risk factors and a risk of an individual having or developing cardiac arrhythmia, and a means to determine the risk of arrhythmia in that individual. In one aspect, the risk factors are cardinal parameters such as, for example, anxiety, depressive disorders, panic attacks, heart palpitations, choking sensation, chest pain, modification of sensory perception, cold sensation in the extremities, sexual dysfunction, decrease of libido, erectile dysfunction, a physical disorder, a mental disorder, neurophysiological abnormalities, brain abnormality, seizures and their frequency, syncope; and unexplained falls. It is contemplated that the apparatus is a smart phone, a smart watch, a tablet computer, or other hand-held computer. It is also contemplated that the data is stored within the apparatus or in a cloud-based storage means. It is also contemplated that the sensor for measuring walking distance and walking speed is a global positioning system, an accelerometer and a position sensor. It is also contemplated that the data memory comprises a program for comparing the one or more measured walking speed with the one or more reference value, and a program for transmitting a result of the comparison to the display.

BRIEF DESCRIPTION OF THE DRAWINGS

These and other features, aspects and advantages of the present invention will become better understood with regard to the following description, appended claims, and accompanying figures where:

DETAILED DESCRIPTION

As used herein, the abbreviation VA refers to a first speed, and is measured by the user walking at the user's usual speed.

As used herein, the abbreviation VB refers to a second speed, and is measured by the user walking at the fastest speed possible without running.

The abbreviation VC as used herein refers to the fast walking speed measured in conjunction with the user performing a cognitive task.

VAref value refers to a reference value from either a normal or abnormal individual and is the measurement taken by the user walking at usual speed VA.

The VBref value refers to a reference value from either a normal or abnormal individual and is the measurement taken by the user walking at fast speed VB.

The VCref value refers to a reference value from either a normal or abnormal individual and is the measurement taken while the user walks fast while performing a cognitive task.

Vequ is the measure of the lateral and/or anteroposterior vertical deviation of the individual, indicative of balance.

Vequref refers to a reference value from either a normal or abnormal individual the lateral and/or anteroposterior vertical deviation of the individual, indicative of balance.

D1 is the difference between calculated or measured VB and VA, and measures the ability of the user to accelerate the user's walking speed.

The abbreviation D1ref refers to the value of the average of the differences between VBref and VAref.

the term "cardinal parameter" is one or more risk factors associated with an individual having or developing cardiac arrhythmia.

Figure 1:
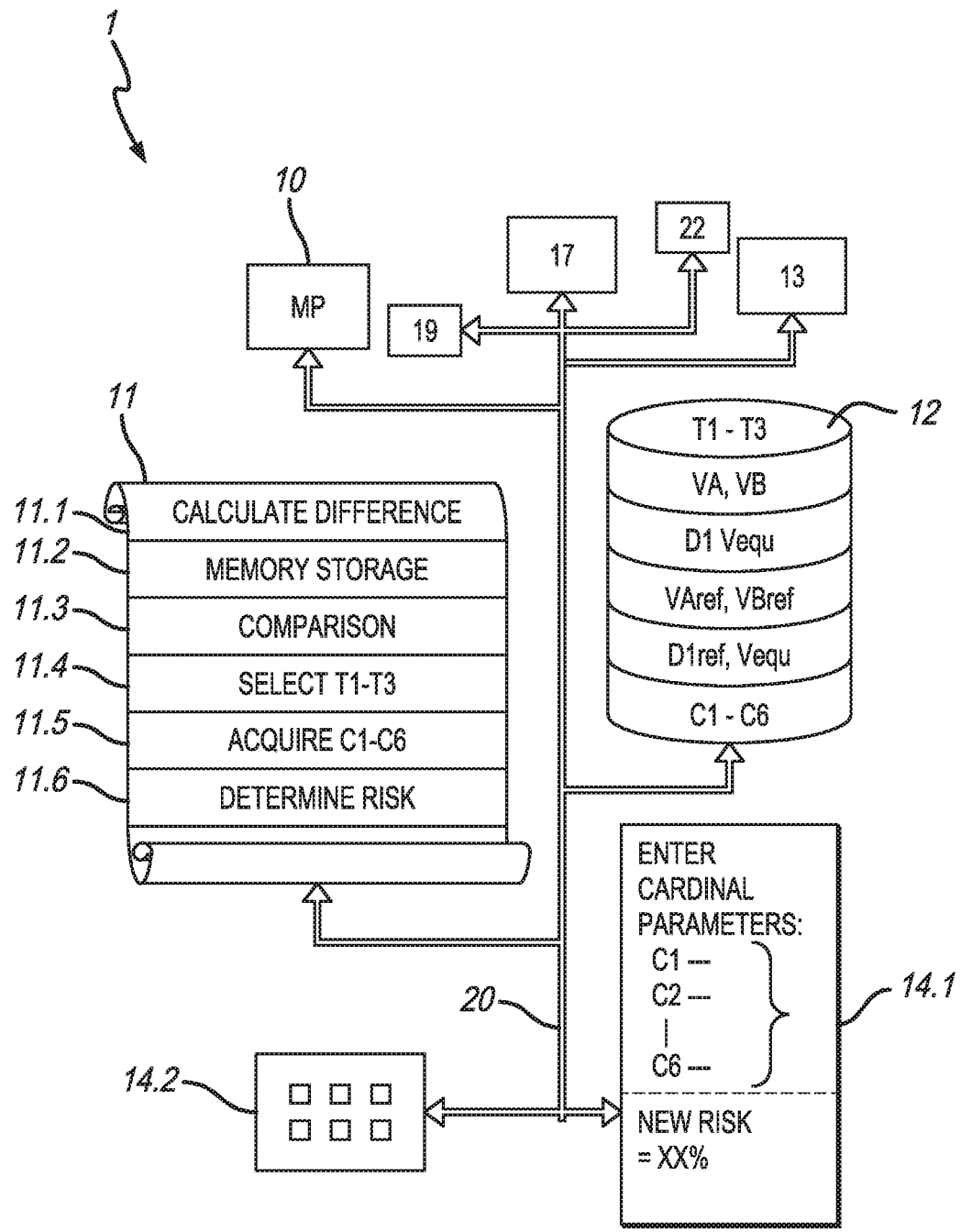
FIG. 1 is a schematic representation of a system for determining the risk of an individual having or developing cardiac arrhythmia according to the invention.

FIG. 1 shows a system 1 according to the present invention for use in determining the risk of an individual having or developing cardiac arrhythmia and its related disorders, including cognitive decline or dementia, stroke, cerebrovascular disease, coronary artery disease. The system 1 comprises a microprocessor 10, a program memory 11, and a data memory 12. There is also a sensor 13 for measuring speed and its corresponding cognitive performances/motivation level, and a man-machine interface 14 formed by a data input display 14.1 and 14.2, such as, for example, input via a keyboard. These elements are interconnected via a data bus 20. Other components 17, 19, 22 can also be added to the system.

The sensor 13 may be a sensor to measure speed, such as, for example, an accelerometer and a position sensor, or a GPS type sensor. Alternatively, the sensor 13 may be a pedometer, a mat with sensors, or a smart shoe. The interface 14 may be, for example, an LED display, a screen, or a buzzer.

The sensor 13 measures the user's walking speed during at least two different types of operation. The first operation uses a first speed VA, which is calculated by the user walking at the user's usual speed for a certain distance and turning once.

In one example, VA is calculated by the user walking at the user's usual speed on a flat surface for a total of 50 meters (25 meters back and forth with one turn). The distance could be shorter or longer depending on the available walking space.

The sensor 13 also measures the user's second speed VB, which is measured by the user walking at the fastest speed possible without running on the same path in the same conditions as the VA measurement was taken.

Additionally, VC, which is measured as the walking speed performed in conjunction with one or more cognitive tasks may be used, as described in patent application number EP12700462, incorporated by reference herein. By increasing the difficulty of the cognitive task, it is possible to detect abnormalities of finer performance, thereby increasing the sensitivity of the test.

The program memory 11 also includes a program to calculate D1, which is the differential speed between VA and VB, shown in FIG. 1 as 11.1, which measures the ability of the user to accelerate the user's walking speed.

In operation, the data memory 12 stores at least two reference values, VAref, VBref, each corresponding to a walking speed. The VAref value is associated with the measurement of the user walking at usual speed VA. The VBref value is associated with the measurement of the user walking at fast speed VB. VCref is associated with the reference value of the user walking at a fast speed while performing a cognitive task. The data memory 12 also stores at least one differential reference threshold D1ref, which is the value of the average of the differences between VBref and VAref. Additionally, the difference between VC and VA is also stored. The data memory 12 also stores alternative reference values, VequRef, for the lateral and/or anteroposterior vertical deviation of the individual, indicative of balance.

A program 11.2 in the memory 12 stores the values of VA, VB, VC, and D1 values, as well as the measured values for Vequ. Vequ can be measured, for example, by a gyroscope or accelerometer.

Figure 2:
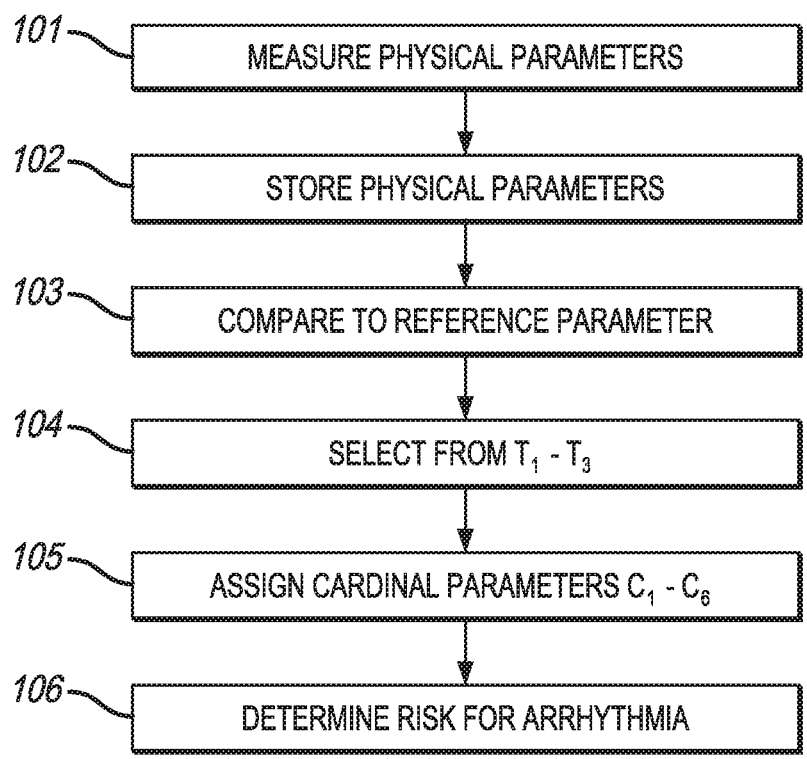
FIG. 2 is a diagram of the steps of the method for determining the risk of an individual having or developing cardiac arrhythmia according to the invention.

The system described herein is an application that can be used to determine an individual user's risk factors for developing cardiac arrhythmia or cognitive disorders. FIG. 2 shows a diagram of the steps of the method of the invention. First, the physical parameters of the individual are measured 101, including VA, VB, and VC. The physical parameter measurements are stored 102, and compared to reference physical parameters 103 such as VAref, VBref, and VCref. The cardinal parameters are selected from the data shown in FIGS. 3A-3C 104, signified by T1, T2, and T3, and cardinal parameters C-C6 are assigned 105. Using the difference between the reference parameters and the measured physical parameters, as well as the number of cardinal parameters, the risk for the individual developing cardiac arrhythmia is determined 106.

Figure 3A:
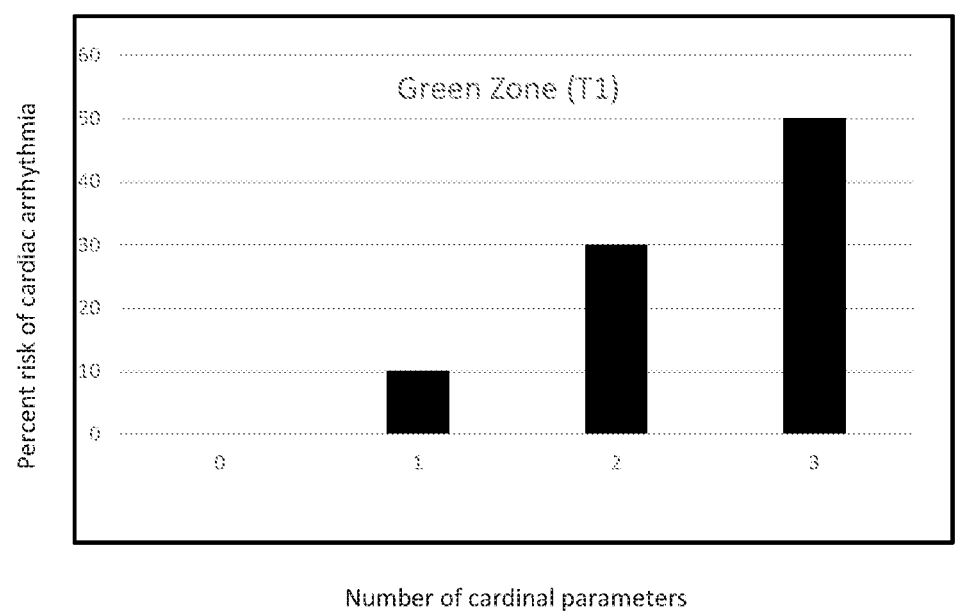
FIGS. 3A-3C depict the data used in the process according to the invention which establishes a correspondence between the number of cardinal signs exhibited by an individual and the risk of an individual having or developing cardiac arrhythmia.
Figure 3B:
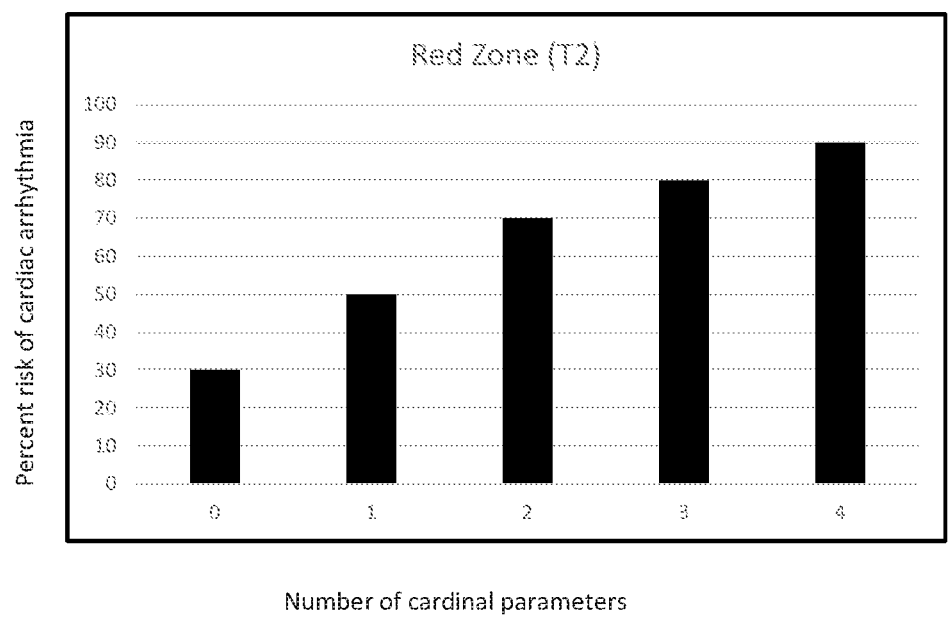

FIGS. 3A-3B are indicative of the relationship between the risk of cardiac arrhythmia and the number of cardinal parameters in an individual. The relationship is used in the method according to the present invention in order to establish a correspondence between the number of cardinal signs exhibited by an individual and the risk of an individual having or developing cardiac arrhythmia. When associated with the risk factors, including cardinal parameters, as described below, the risk of unsuspected or underestimated cardiac arrhythmias can be determined.

Figure 3C:
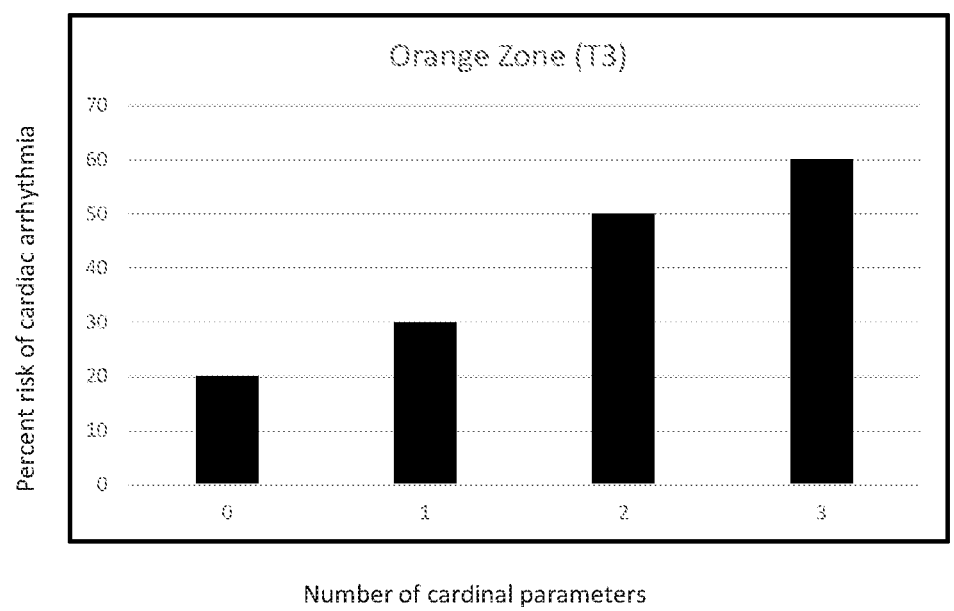
Figures 4A, 4B:
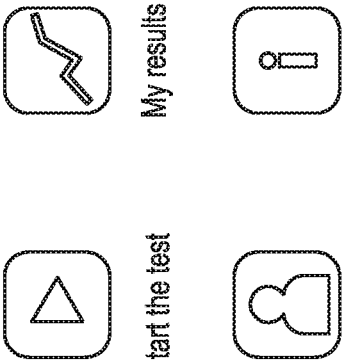
FIGS. 4A-4H depict screenshots of an application that can be performed on a smartphone or other device pursuant to one embodiment of the invention.

A device, such as a smart phone, smart watch, tablet computer or the like collects data from the user, as shown in FIG. 4A. The data memory 12 stores various parameters used to indicate the level of risk of arrhythmia. The percent risk of an individual developing cardiac arrhythmia is shown in FIGS. 3A-3C. The percentages are associated with the result of the comparison between the walking speeds VA and VB, reference values VAref, VBref and D1ref, D1, and if applicable, one or more balance disorders.

Risk factors for unsuspected or underestimated cardiac arrhythmias can be entered into the system by the user through the HMI interface 14. For example, the user can enter information corresponding to several parameters, termed cardinal parameters. Cardinal parameters may include, but are not limited to: the presence or history of anxiety and/or depressive disorders, sensory as well as the sensation of cold extremity modification, sexual and/or libido disorders, the existence of at least one other physical and/or mental illness, the existence of electro-neurophysiological or brain anomalies, the presence and frequency of seizures, syncopes, and falls.

The risk factor for an individual cardinal parameter is important; however, the risk factor increases greatly depending on the number of associated cardinal parameters. These cardinal parameters are as follows:

C1—the presence or history of anxiety and/or depressive disorders such as panic described in DSM4 (including palpitations, choking sensation and chest pain, etc.) and modification of sensory perception and cold sensation in the extremities, sexual dysfunction, and decrease of libido or erectile dysfunction;

C2—the existence of at least one other known physical and/or mental pathology;

C3—the existence of neurophysiological abnormalities (EEG, evoked potentials, etc.) and/or brain abnormality (MRI, CT, etc.);

C4—the presence of seizures and their frequency;

C5—the presence of syncope; and

C6— the existence of unexplained falls with or without fractures and their frequency.

The risk of having or developing cardiac arrhythmia increases with the presence of cardinal parameters: one cardinal parameter increases the risk of cardiac arrhythmia to 50%, two cardinal parameters increases the risk of cardiac arrhythmia to 70%, and three cardinal parameters increases the risk of cardiac arrhythmia to 80%. FIG. 2 shows one aspect of the invention and describes the steps that are taken on a smartphone or other device in order to determine the risk of an individual having or developing cardiac arrhythmia or dementia according to the present invention. The first step 101 is to measure physical parameters, in this case the user's walking speeds (usual walking VA and fast walking VB) obtained by the sensor 13, and the differential D1 calculated by 11.1. The equilibrium values Vequ are also obtained. In a step 102, the physical parameters VA, VB, and Vequ D1 are stored in the data memory 12 within the program 11.2.

In step 103, the measured physical parameters are compared 11.3 program, with the physical parameters of reference VAref, VBref, D1ref and VequRef. The result of this comparison categorizes the individual into the different zones as described below and in FIGS. 3A-3C (green, red or orange).

In step 104, the program then selects 11.4, the zone corresponding to the area where the individual falls under.

In step 105, the individual's information is entered or acquired 11.5 via the HMI device 14. The information reflects the user's background and/or the presence of cardinal parameters corresponding to C1-C6. The program stores the presence or absence of these cardinal parameters C1-C6 in the memory 12.

In step 106, the 11.6 program then determines the risk of the user having or developing cardiac arrhythmia using the number of parameters associated cardinals C1-C6 from the different zone.

The different zones are ascertained as follows. FIG. 3A shows a graph referred to herein as "green," or "T1," which corresponds to the user's measured values of walking speeds VA, VB, a differential value D1, and Vequ relative to normal reference values VAref, VBref, D1ref, and optionally VequRef. The values VA, VB and D1 are defined as normal, or green, when all of the values are greater than or equal to the reference values VAref, VBref, and D1ref.

FIG. 3B shows a graph referred to herein as "red," or "T2," which corresponds to the user's measured values of walking speeds VA, VB a differential value D1, and Vequ relative to abnormal reference values VAref, VBref, D1ref and optionally VequRef. The values VA, VB and D1 are abnormal, or in the red zone, when all of the values are greater than one standard deviation lower than the normal reference values. Additionally, an individual is placed in the red zone if the individual has four or more abnormal cardinal parameters. As can be seen, an individual in the red zone with four cardinal parameters has a 90% chance of having or developing cardiac arrhythmia.

FIG. 3C shows a graph referred to herein as "orange," or "T3," which corresponds to the measured values of walking speeds VA, VB, a differential value D1, and Vequ relative to abnormal or uncertain reference values VAref, VBref, D1ref, and optionally VequRef. The values VA, VB and D1 are abnormal/uncertain, or in the orange zone, when all of the values are one standard deviation lower than the normal reference values. Additionally, an individual is placed in the orange zone if two to four cardinal parameters are abnormal. As can be seen, an individual in the orange zone with two cardinal parameters has a 50% chance of having or developing cardiac arrhythmia. An individual in the orange zone with three cardinal parameters has a 60% chance of having or developing cardiac arrhythmia.

Patent Application EP12700462 contains a description of how different reference values are determined from a group of people. In one example, the threshold value for a normal VAref was 1.4 m/s+/−0.1 m/s. The threshold value for a normal VBref was 1.70 m/s+/−0.1 m/s. The threshold value for a normal D1ref, the variation between these speeds, is 0.3 m/s.

The normal user has a calculated walking speed which is in a normal, or green range. As shown in FIG. 3A, the value corresponding to the epidemiology in the normal population for the risk of cardiac arrhythmia is shown. As expected from a normal population with no cardinal parameters, there is very low risk of having or developing cardiac arrhythmia. However, the risk of cardiac arrhythmia increases with the presence of cardinal parameters: one cardinal parameter increases the risk of cardiac arrhythmia to 10%, two cardinal parameters increases the risk of cardiac arrhythmia to 30%, and three or more cardinal parameters increases the risk of cardiac arrhythmia to 50%.

A user with an extremely increased risk of cardiac arrhythmia, or red range, has a calculated walking speed which is below normal. As shown in FIG. 3B, the data reflects that those individuals start at 30% risk of having or developing cardiac arrhythmia. The risk of cardiac arrhythmia increases with the presence of cardinal parameters: one cardinal parameter increases the risk of cardiac arrhythmia to 50%, two cardinal parameters increases the risk of cardiac arrhythmia to 70%, three cardinal parameters increases the risk of cardiac arrhythmia to 80%, and four cardinal parameters increases the risk of cardiac arrhythmia to 90%.

A user with an increased risk of cardiac arrhythmia has a calculated walking speed which is below normal speed but not abnormal, and is classified as having an uncertain risk of having or developing cardiac arrhythmia. As shown in FIG. 3C, the data reflects those individuals with an abnormal or uncertain risk of cardiac arrhythmia starting at a 20% risk of cardiac arrhythmia (orange zone). The risk of cardiac arrhythmia increases with the presence of cardinal parameters: one cardinal parameter increases the risk of cardiac arrhythmia to 30%, two cardinal parameters increases the risk of cardiac arrhythmia to 50%, and three cardinal parameters increases the risk of cardiac arrhythmia to 60%.

Figure 4D:
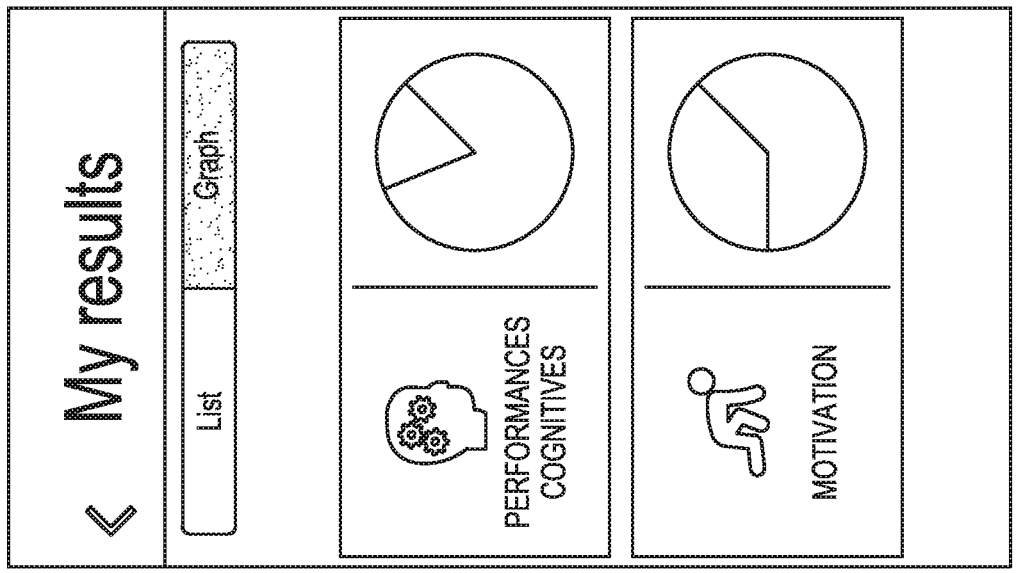
Figure 4C:
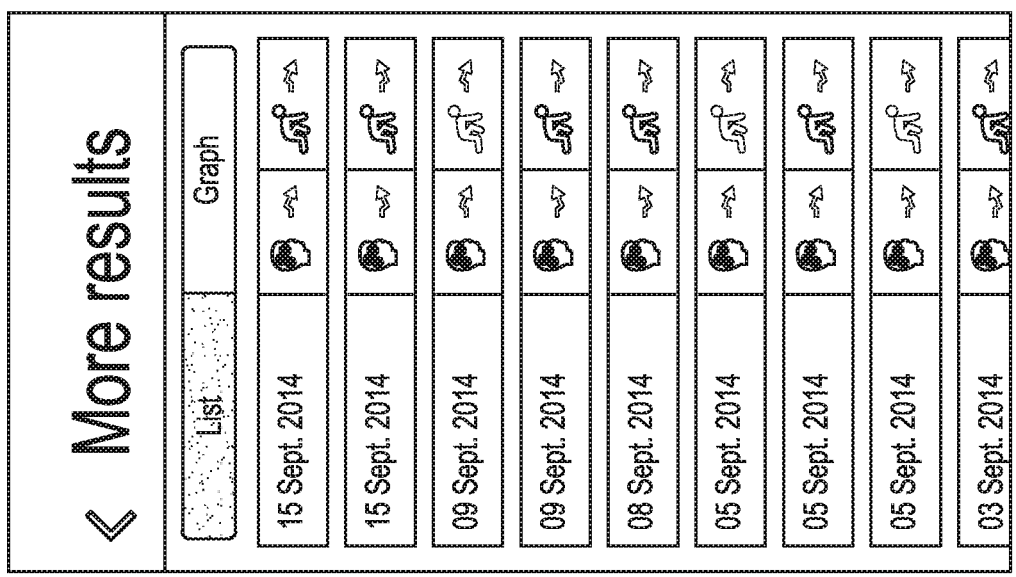
Figure 4F:
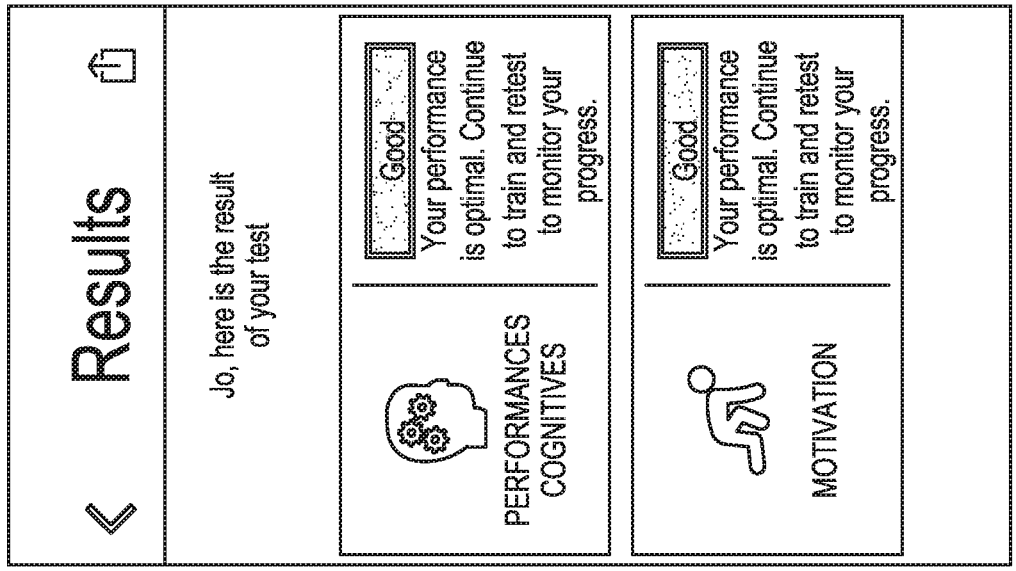
Figure 4E:
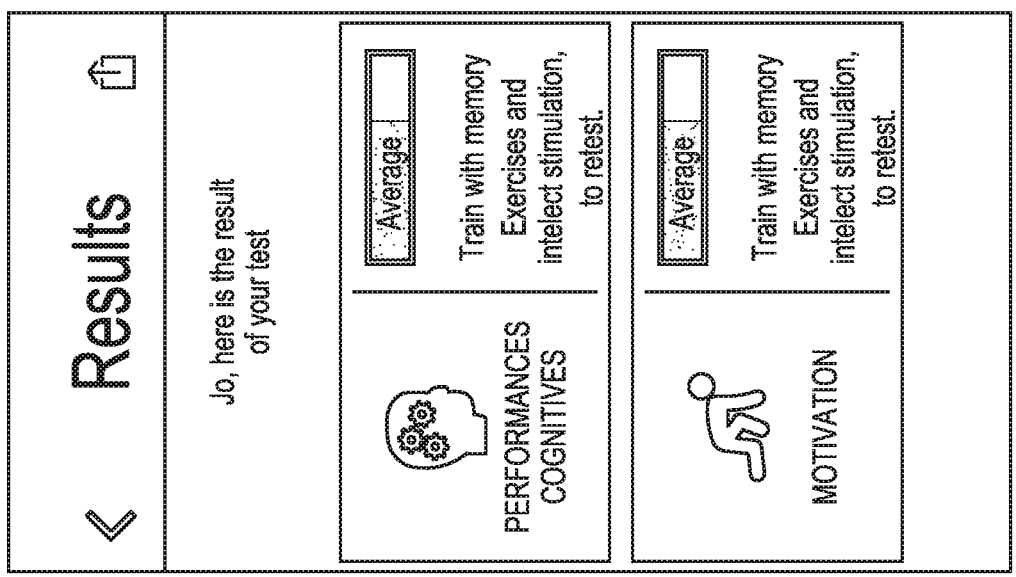
Figure 4H:
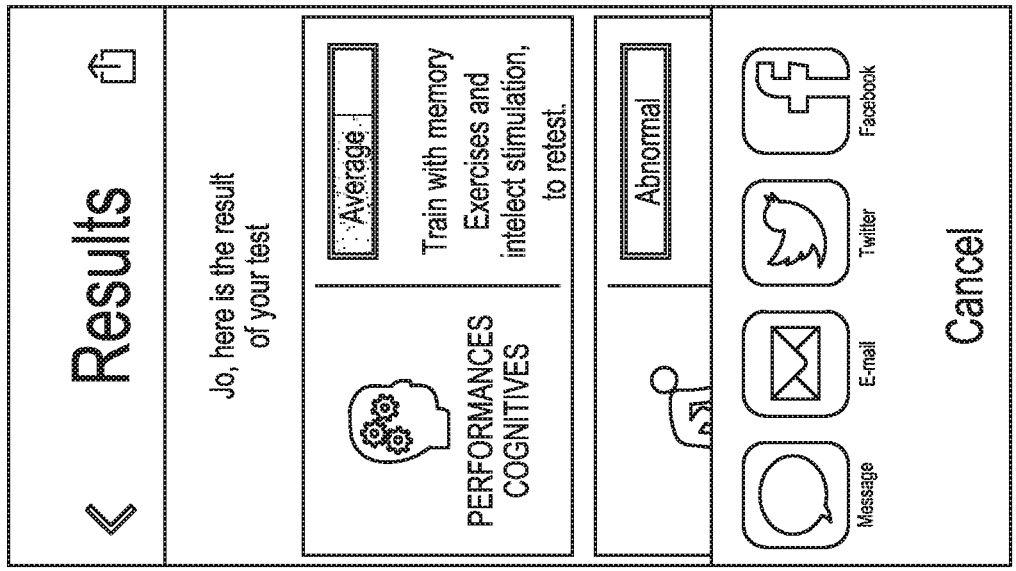
Figure 4G:
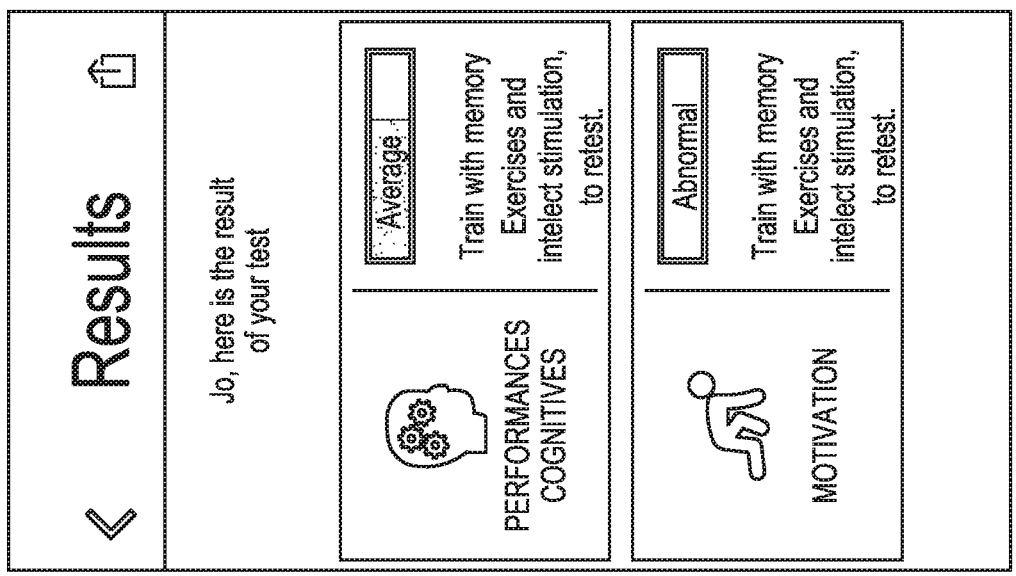

According to one aspect of the invention, if the speed of calculated walk is lower than the absolute threshold of normality, the display emits a red-colored display which reads "unfavorable" as shown in FIG. 4G. This result indicates that the user has abnormal motor, cognitive and motivational performance and might be at risk for development of cardiac arrhythmia.

The invention uses a global index, Iglob, to quantify the cardinal parameters. Iglob is calculated by the sum of the values of the cardinal parameters, C1-C6 (0-180), the value being proportional to the size of the disorder. The different zones (green, red, or orange as shown in FIGS. 3A-3C) can be quantified, and establishes a relationship between the risk of arrhythmia and global index Iglob so it is possible to determine from the calculated Iglob the risk of associated cardiac arrhythmia.

According to another embodiment of the invention, the cardinal parameters are quantified. In this case, the first cardinal parameter C1 is quantified by example by a value of from 0 to 20, the value being proportional to the size of the disorder. The second cardinal parameter C2 is quantified by a value equal to the number of weighted by a particular value, such as 10, for cardiac history or other associated pathologies (0-20). The third cardinal parameter C3 is quantified by a value ranging from 0-40 (the value of 20 is assigned if there is one anomaly and the value of 40 assigned if multiple defects exist). The fourth cardinal parameter C4 is quantified using a subjective value from a scale measuring the intensity and frequency of the disorder. The value of the fourth parameter is, for example, 5 if the occurrence is rare (1 or 2 dizzy spells per year), 10 if the dizzy spells occur weekly, or 20 if the dizzy spells occur daily. The fifth cardinal parameter C5 is quantified by a value of 20 for one to 40 depending on the frequency of occurrence of syncope occurrence. The sixth cardinal parameter C6 is quantified by a value of 20 for one fall and 40 for more than one fall. (0-40)

FIGS. 4A-4H depict screenshots of an example of an application of the invention showing implementation of the system of the invention on a smartphone device. FIG. 4A shows the homescreen of the application where a user may select from the options "start the test," "see my results," "see my profile," or "information." FIG. 4B shows a screenshot of the user's profile input. FIG. 4C shows a list of the history of the user and their test results. FIG. 4D shows a "my results" page. FIG. 4E shows an example after the user has completed the test, "here is the result of your test," in this screenshot, the applicant scored "average." FIG. 4F shows another example after the user has completed the test, "here is the result of your test," in this screenshot, the applicant scored "good." FIG. 4G shows another example after the user has completed the test, "here is the result of your test," in this screenshot, the applicant scored "abnormal." FIG. 4H shows where the user may share his test results on social media such as, for example, Twitter, Facebook, Messenger, etc.

In addition to using the system and device for detecting the risk of cardiac arrhythmias in an individual, the invention also includes a system and device for detecting the risk of abnormal cognitive performance or dementia in the user using the walking speed of the user. The use of the system for the detection of the risk of developing abnormal cognitive performance uses the relationship described above correlating walking speed to the risk of developing abnormal cognitive performance.

The method for detecting the abnormal cognitive performance of an individual comprises the following steps:
1) calculating global psychometric-calculate scores for each individual in a group of healthy individuals with an age between 18 and 65 years;
2) measuring the walking speeds of all the individuals in the group;
3) establishing, by a statistical method, a relationship between the walking speed and the psychometric global score individuals of the group;
4) calculating a first threshold value walking speed, said absolute normal threshold, from a data set collected from a sample of individuals;
5) transmitting the first threshold value into a data memory;
6) measuring the walking speed of an individual;
7) comparing the measured walking speed with the first threshold value; and
8) issuing an audible and/or visual signal according to the comparison result.

EXAMPLE

The system 1 was used in 110 patients who had at least three extra-cardiac conditions corresponding to the cardinal parameters C1-C6. After measuring walking speed VA-VB, the orange or red zone was selected based on the difference between VA and VB. In all cases, the physical parameters were more than one standard deviation below the mean of the normal reference values.

Given that these 110 patients had at least three cardinal parameters, they were 60% (for orange zone) and 80% (for the red zone) more likely than a normal individual to have cardiac arrhythmia. This risk was subsequently confirmed by further investigation. After an objective review of outpatient records, the data showed 60 of the 110 patients had evidence of heart rhythm disorders.

Thirty-eight of the patients had a pacemaker implanted, and two others patients were treated by radio frequency. The 40 treated patients had a normal evolution with no complications. The other subjects were not treated. Ten of the 70 patients had a stroke and 25 patients developed dementia. However, there were 10 cases of stroke, 25 cases of dementia, and 8 cases of sudden death among the other 70 patients who had no further treatment or follow-up. The percentage of sudden death represents 11.5% of the 70 patients over a period of 15 years. Reduced to one year, this corresponds to an epidemiology of 0.76%. In comparison, the epidemiology of sudden death in a population with no overt cardiac disorder was 0.25 per thousand. Thus, the risk of sudden death was 30 times higher in the population with the detected extra-cardiac cardinal parameters.

In addition, the following two cases below are typical illustrations of sudden cardiac death presenting with extra cardiac signs of unrecognized or underestimated cardiac arrhythmia. Two women, 41 and 49 years old, had a history of anxiety and depressive disorders, and were diagnosed with panic disorder and benign vasovagal syncope. They also had four cardinal parameters, including unexplained falls, dizzy spells, and palpitations, and slight decrease of EEG alpha rhythm power. A thorough cardiac investigation was deemed unnecessary by their cardiologists. However, both women died in their sleep of sudden cardiac death.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Although the present invention has been described with a degree of particularity, it is understood that the present disclosure has been made by way of example and that other versions are possible. As various changes could be made in the above description without departing from the scope of the invention, it is intended that all matter contained in the above description or shown in the accompanying drawings shall be illustrative and not used in a limiting sense. The spirit and scope of the appended claims should not be limited to the description of the preferred versions contained in this disclosure.

What is claimed is:
1. An apparatus for determining a risk of arrhythmia in an individual comprising:
a) an electronic apparatus with a display;
b) a sensor used to measure one or more physical parameters in the individual, the physical parameters chosen from the group comprising the individual's usual walking speed (VA), the individual's fast walking speed (VB), the individual's fast walking speed while the user performs a cognitive task (VC), and the individual's equilibrium parameters (Vequ), wherein the sensor for measuring walking distance and walking speed is selected from the group consisting of a global positioning system, an accelerometer, a pedometer, a mat with sensors, or a smart shoe;
c) a means for storing the physical parameters from (a) in a data memory;
d) a means to compare the measured physical parameters from (a) with reference physical parameters chosen from the group comprising usual walking speed refer- ence (VAref), fast walking speed reference (VBref), and an equilibrium parameter reference (VequRef);
e) a means for inputting the number of risk factors present in the individual;
f) a means to determine the statistical correspondence between one or more risk factors and a risk of an individual having or developing cardiac arrhythmia; and
g) a means to determine the risk of arrhythmia in that individual using the numbers from (a) through (e).

2. A method for detecting the risk of an individual having or developing cardiac arrhythmia comprising:
a) measuring one or more physical parameters in the individual using the apparatus of claim 1, the physical parameters chosen from the group comprising the individual's usual walking speed (VA), the individual's fast walking speed (VB), the individual's fast walking speed while the user performs a cognitive task (VC), and the individual's equilibrium parameters (Vequ);
b) comparing the one or more physical parameters alone or in combination with physical parameters reference values (VAref, VBref, VCref, D1ref);
c) establishing a statistical correspondence between risk factors and a risk of an individual having or developing cardiac arrhythmia;
d) quantifying the number of risk factors in the individual; and
e) calculating the risk of an individual having or developing cardiac arrhythmia based on the individual's walking speed and number of risk factors, thereby detecting the risk of an individual having or developing cardiac arrhythmia.

3. The method of claim 2 wherein the risk factors comprise cardinal parameters.

4. The method of claim 3 wherein the cardinal parameters are selected from the group comprising anxiety, depressive disorders, panic attacks, heart palpitations, choking sensation, chest pain, modification of sensory perception, cold sensation in the extremities, sexual dysfunction, decrease of libido, erectile dysfunction, a physical disorder, a mental disorder, neurophysiological abnormalities, brain abnormality, seizures and their frequency, syncope; and unexplained falls.

5. The method of claim 2, wherein the statistical correspondence between the risk factors and a risk of an individual having or developing cardiac arrhythmia is taken from the Iglob index.

6. The apparatus of claim 1 wherein the risk factors comprise cardinal parameters.

7. The apparatus of claim 6 wherein the cardinal parameters are selected from the group comprising anxiety, depressive disorders, panic attacks, heart palpitations, choking sensation, chest pain, modification of sensory perception, cold sensation in the extremities, sexual dysfunction, decrease of libido, erectile dysfunction, a physical disorder, a mental disorder, neurophysiological abnormalities, brain abnormality, seizures and their frequency, syncope; and unexplained falls.

8. The apparatus of claim 1 wherein the electronic apparatus is a smart phone, a smart watch, a tablet computer, or other hand-held computer.

9. The apparatus of claim 1 wherein the data memory is stored within the apparatus or in a cloud-based storage means.

10. The apparatus of claim 1 wherein the data memory comprises a program for comparing the one or more measured walking speed with the one or more reference value, and a program for transmitting a result of the comparison to the display.

* * * * *